United States Patent [19]

Pietikäinen

[11] Patent Number: 5,385,508
[45] Date of Patent: Jan. 31, 1995

[54] ASSEMBLY FOR GUIDING DIFFERENT KINDS OF EQUIPMENT AROUND ELONGATED OBJECTS

[75] Inventor: Lauri Pietikäinen, Helsinki, Finland
[73] Assignee: Imatran Voima Oy, Helsinki, Finland
[21] Appl. No.: 80,127
[22] Filed: Jun. 23, 1993
[30] Foreign Application Priority Data Jun. 24, 1992 [FI] Finland .................................. 922943

[51] Int. Cl.6 ............................................. F16H 7/00
[52] U.S. Cl. ...................................... 474/148; 474/134
[58] Field of Search ........................ 474/148, 133–135

[56] References Cited

U.S. PATENT DOCUMENTS 1,320,044 10/1919 Heaney .................................. 474/134
1,869,692 8/1932 Horner ............................... 474/134 X
2,090,423 8/1937 Morrell ............................. 474/134 X Primary Examiner—Michael Powell Buiz

[57] ABSTRACT

An assembly for guiding different types of inspection and machining apparatuses around permanently installed pipes and shafts in power plants and similar locations. Such assemblies are used for guiding equipment employed in the inspection and machining of elongated objects with a circular cross section around said objects. According to the invention the assembly is mounted around the object by a belt which is tightened between two belt pulleys so as to embrace the object. The belt pulleys are mounted on a body part to both sides of a drive motor that drives both belt pulleys synchronously via gear wheels. The mounting of the assembly on the object to be inspected is extremely rapid.

11 Claims, 4 Drawing Sheets

ASSEMBLY FOR GUIDING DIFFERENT KINDS OF EQUIPMENT AROUND ELONGATED OBJECTS

BACKGROUND OF THE INVENTION

1. Field of the Invention The present invention concerns an assembly for guiding different kinds of inspection and machining equipment around permanently installed pipes and shafts in power plants and similar locations.

2. Description of Background Art

Assemblies related to the present invention are used for guiding equipment employed in the inspection and machining of elongated objects with a circular cross section around said objects. Such equipment includes, ultrasound transducers, polishing/grinding/cutting equipment, welding torches and similar equipment. The principal application of such equipment is, e.g., in the scheduled inspections of power plant piping where the ultrasonic techniques are employed for monitoring the wear of piping walls during use. In such locations the guiding assemblies must be fitted around permanently installed piping, which prevents the mounting of said assemblies around a pipe by pushing them over the pipe from the end of the pipe, but rather, the mounting and guiding assemblies must be either permanently mounted, or alternatively, they must be capable of opening for mounting around the pipe. As the objects to be inspected are located in hard-to-reach places, the mounting and guiding assemblies must be easily mountable around the pipe.

Conventionally, these applications employ different types of segmentally linked guide rails forming a circular band that can be intimately fitted around the pipe with the help of various adjustable mounting elements. Standard equipment is then mounted on the rail of the segment which guides the equipment and provides a counter surface for the power drive elements of the guiding assembly. Different types of chains and gear elements are used as the power drive elements.

GB patent application 2,012,047 discloses an assembly comprised of a guide rail, which is mountable around the pipe, and further has cylindrical guide wheels with a center groove for the rail that are adapted to run supported by the guide rail. Supported by the wheels is adapted a transfer carriage movable by means of a chain drive. Different types of transducers and machining equipment, e.g., a welding torch, can be mounted to the transfer carriage. The guide rail is permanently mounted onto the pipe, so it cannot be transferred to different points of use, but rather, each point to be inspected must be provided with a separate, permanently fixed guide rail.

U.S. Pat. No. 4,515,018 describes an assembly in which the actual guide rail is mounted securely with the help of a separate support element to a suitable position for the measurement. The support element and the guide rail open into two parts which can be threaded around the pipe and fixed by means of locking elements. The inner perimeter of the support element has clamping means whose position can be adjusted to adapt the support element around the pipe perimeter. The adjustment span of the clamping means is relatively short, so a single support element cannot serve a larger range of pipe diameters.

The above-described apparatuses have several drawbacks. While the actual inspection procedure can be performed rapidly using fixed-rail apparatuses, the installation of the guide rails to each location to be inspected is cumbersome and expensive. For new inspection sites, such arrangements always necessitate a demanding installation phase as the guide rail must be aligned with a high precision to assure a sufficiently good repeatability of the measurement. For the above-mentioned reasons, fixed rail structures are suited to frequently repeated inspections only. Segmentally linked guiding and mounting structures are hampered by time-consuming installation at each new site. If a preadjusted mounting ring is available for each inspection site, the measurement session is carried out relatively rapidly, while the installation at a new site may take a lot of time. Such a readjustment may be necessary at pipe size transitions. Conventionally, the guiding rail is mounted around the pipe with the help of various clamping means. The adjustment span of such means is invariably small, so piping of varying size must be covered with a large selection of guiding rail assemblies.

SUMMARY AND OBJECTS OF THE INVENTION

It is an object of the present invention to achieve an assembly for the abovedescribed application, suited for easy mounting around pipes and similar elements of different sizes.

The invention is based on mounting the assembly around a pipe by means of a tensionable toothed belt routed over two toothed belt pulleys.

The invention provides significant benefits.

By virtue of the assembly according to the present invention, the need for separate mounting elements is obviated. The mounting of the assembly at the site to be inspected or machined is very rapid, and the assembly can be readily mounted in very tight locations. If the piping is provided with markings for aligning the assembly in repetitive measurements, the repeatability of measurements is good. The function of the assembly is free from any wear effects. Further, the assembly can also be driven around the pipe for an unlimited number of times, up to extension of the interconnect cables of transducers and machining equipment around the pipe. Obviously, the assembly can be powered by a rechargeable battery for certain applications, whereby the interconnect cables are redundant. The cumbersome erection of work platforms for in-site machining of pipes and shafts becomes unnecessary as the assembly can be easily mounted to the site to be machined, and the operator need not support the assembly during machining, allowing him to work on a simple ladder. The drive motor of the assembly can be complemented with a pulse sensor, whereby the measurement coordinate can be readily and repeatably determined during the measurement of, e.g., the thickness profile of a pipe wall.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
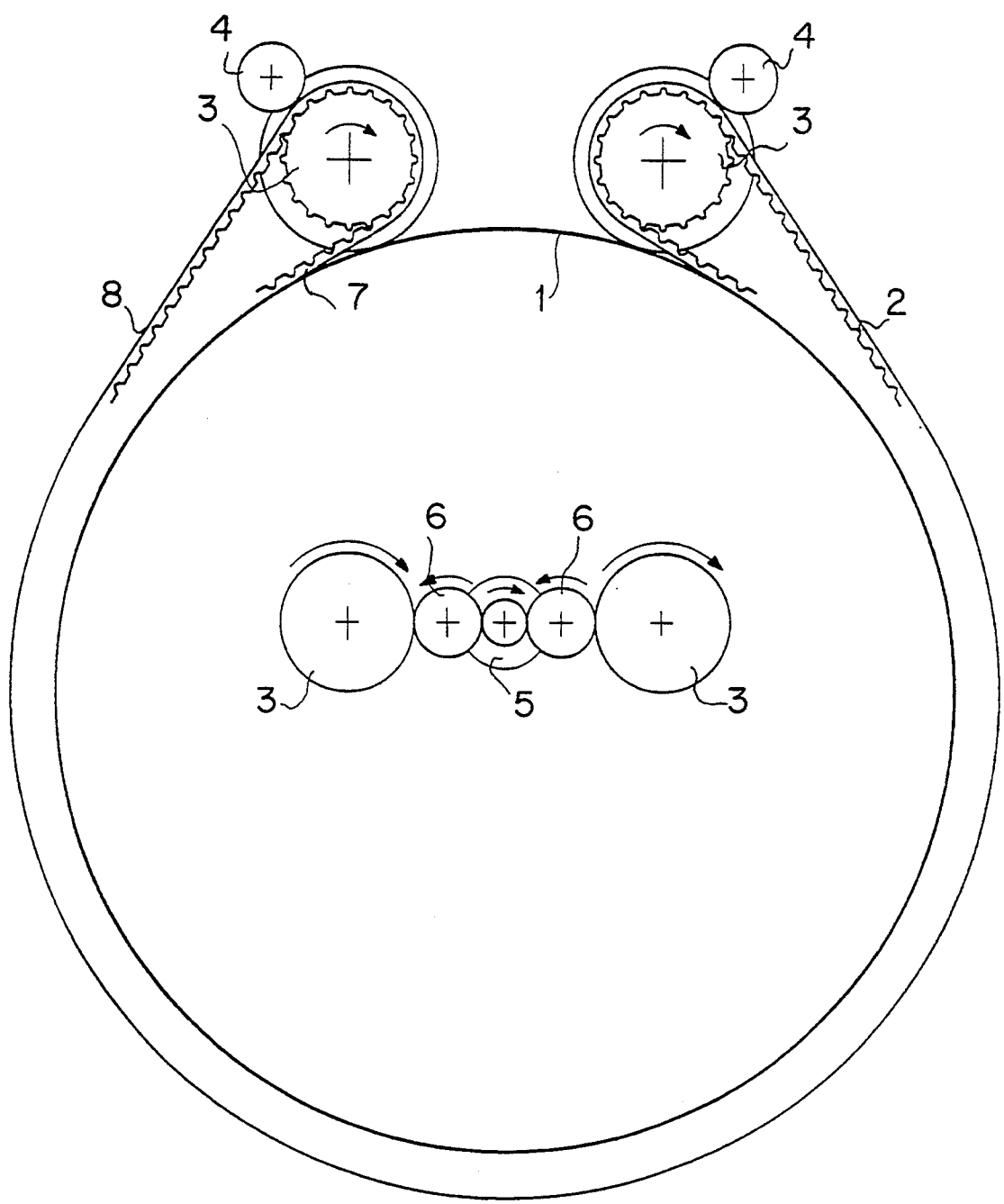
FIG. 1 is schematic view of the operating principle of the assembly according to the invention.

According to FIG. 1, the assembly is mounted around a pipe 1. A toothed belt 2 is routed over a first toothed belt pulley 3, then intimately over the periphery of the pipe 1 and finally over a second toothed belt pulley 3 with the smooth outer side of the belt 2 resting against the pipe 1. This section of the belt forms the inner leg 7 of the belt 2. The belt pulleys 3 are complemented with spring-loaded or lockable guide 4 rollers which compress the belt 2 against the belt pulley 3 so as to prevent slackening of the belt in its first leg 7. From the second belt pulley 3 the belt 2 returns to the first belt pulley 3 forming the freely hanging untensioned outer leg 8 which completes the folded loop of the belt 2.

Additionally, FIG. 1 shows the drive arrangement for the belt pulleys 3. In the gear diagram, the drive motor 5 is adapted between the belt pulleys 3 and the rotational drive of the motor 5 is geared to the belt pulleys 3 via intermediate gear wheels 6. Such an arrangement provides the belt pulleys 3 with synchronized rotational direction and speed. Consequently, the arrangement shown in the diagram is entirely symmetrical, and thus, in the above explanation, permits free interchanging of the functional descriptions of the elements symmetrically located around the center line.

When the assembly is to be mounted around (a pipe 1), the belt 2 is first inserted over the first belt pulley 3 and locked with the help of the guide roller 4. Next, the belt 2 is routed around the pipe 1 and then further inserted over the second belt pulley 3, simultaneously tensioning the inner leg 7 of formed loop tightly against the pipe 1. The belt 2 is locked onto the belt pulley 3 with the help of the guide roller 4, and the excess length of the belt 2 is allowed to sag as a slack loop. During the motion of the assembly, the belt pulleys 3 travel over the toothed belt 2, and the tension of the belt 2, together with the friction of the belt 2 against the pipe 1, keep the assembly stationary even when the guiding assembly is placed to the side of a pipe 1. Thus, the assembly is capable of travelling around the entire perimeter of the pipe 1, making it suitable for use on pipes aligned in any position. However, the belt 1 must be relatively wide to provide sufficient sideways guidance during the movement.

Figure 2:
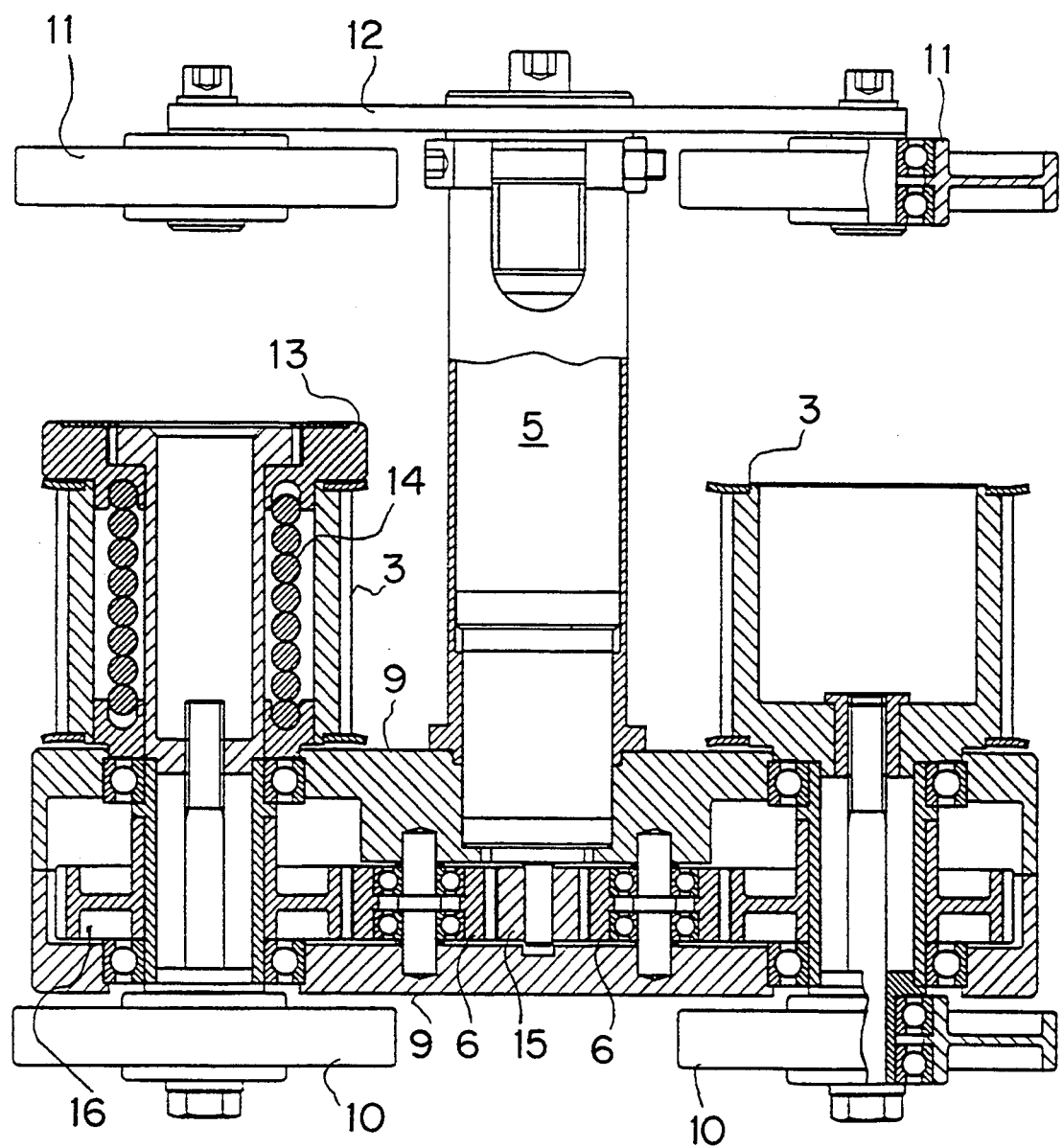
FIG. 2 is a partially sectional longitudinal view of an embodiment according to the invention.
Figure 3:
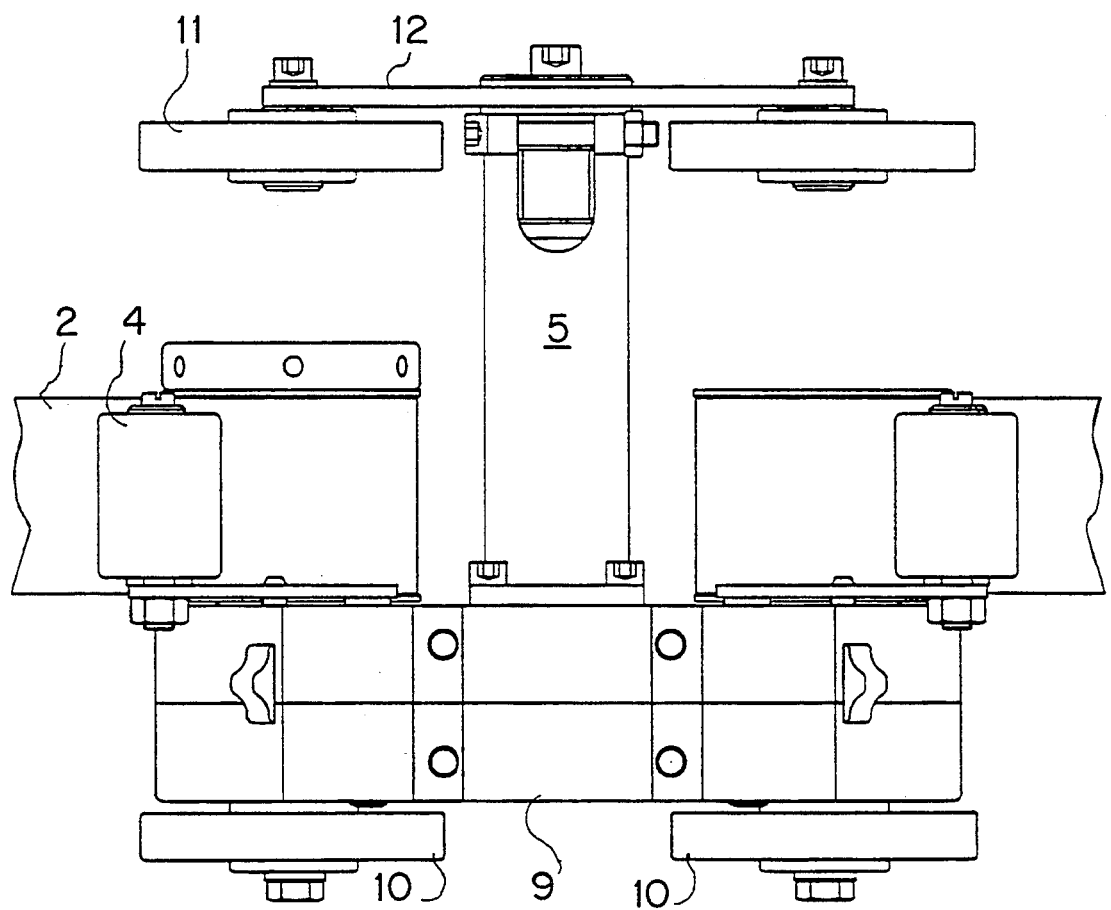
FIG. 3 is a side view of the embodiment shown in FIG. 2.

FIGS. 2 and 3 illustrates in greater detail an embodiment of the present invention. This embodiment of the assembly is constructed on a body comprised of two body parts 9. The drive motor 5 is mounted at the center line of the body 9. The belt pulleys 3 are mounted on shafts on the body 9, to both sides of the motor 5. The drive shaft of the motor 5 has a driving gear wheel 15, with intermediate gear wheels 6 placed to both sides of it. Mounted on the shaft of each belt pulley 3 is a driven gear wheel 16, both of which are in a meshing position with the intermediate gear wheel 6. The transmission chain formed in this manner provides synchronous drive for the belt pulleys 3.

One of the belt pulleys 3 is directly driven via its shaft from the driven gear wheel 16. Between the second belt pulley 3 and its driven gear wheel 16 is adapted a spring-loaded ratchet 13 for belt tensioning during the installation of the belt. The ratchet 13 incorporates a coiled spring 14 whose one end is connected to the belt pulley 3 and the other end via the body of the ratchet 13 to the shaft of the driven gear wheel 16. The ratchet has a dual function in the assembly: firstly, it helps the mounting, and secondly, it assures steady tightness of the belt. After the belt is routed around the pipe during the mounting of the assembly, it is inserted over the belt pulley 3, 13 equipped with the ratchet and locked with the gear teeth. The belt is next tensioned properly by either pulling from the slack end of the belt, or attentively, tightening the ratchet with a wrench, whereby the pawl mechanism of the ratchet 13 permits rotation of the belt pulley 3 and tensioning of the spring 14 of the ratchet 13. Thus, the mounting and tensioning of the belt is made extremely easy. On the other hand, when the assembly is travelling on the pipe outer surface, the spring 14 of the ratchet 13 permits a small tolerance in the synchronized motion of the belt pulley 3. If the pipe outer surface has depressions, the spring 14 rotates the belt pulley 3 and thus tensions the belt. On the other hand, if the pipe outer surface has bumps, the spring provides for a small allowance in the inner leg length of the belt spanned between belt pulleys.

The assembly shown in FIG. 2 travels on the pipe periphery supported by support wheels 10 and 11. The first support wheels 10 are mounted on the same shafts as the driven gear wheels 16, making said support wheels 10 to rotate at the same speed as the belt pulleys 3. The second support wheels 11 are mounted to the ends of a lever 12 which is pivoted at its center to the end of the body of the drive motor 5. The center-pivoted lever 12 is mounted to the body of the motor 5 by a pivotal joint which permits the rotation of the lever 12 about its pivoted center point. By virtue of the pivotal motion of the lever 12, the support wheels 11 can be turned aside during the insertion of the belt over the belt pulleys, which makes the insertion of the belt easy. Moreover, the pivotally moving wheels 11 can better follow the pipe outer surface.

Figure 4:
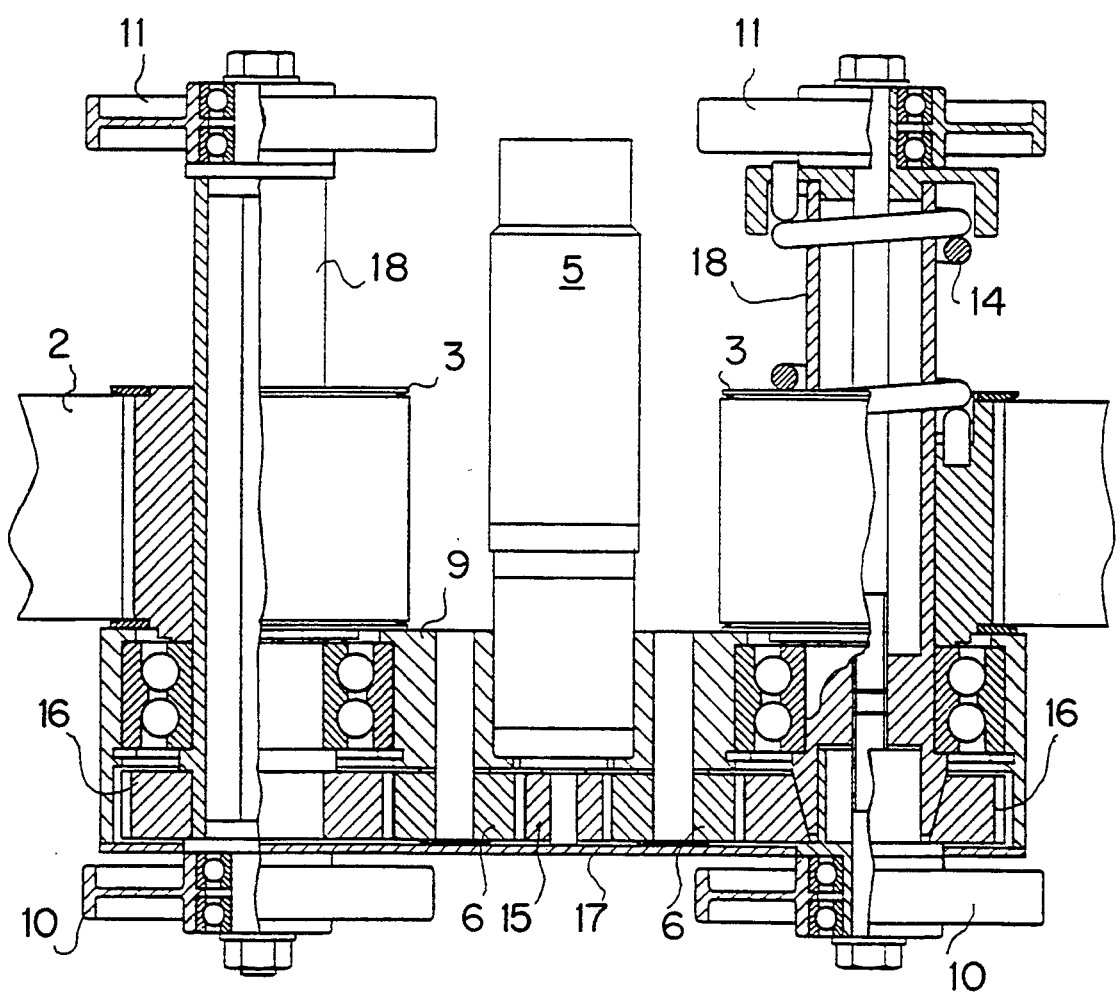
FIG. 4 is a partial sectional longitudinal view of another embodiment according to the present invention.

FIG. 4 shows another embodiment of the invention. This assembly is constructed into a one-piece body 9. The body 9 is closed with the help of a cover plate 17. The placement of the elements and drive arrangements are similar to those of the above-described embodiment. Equivalently, the first support wheels 10 are mounted to the common shaft 18 of the driven gear wheels 16 and the belt pulleys 3. The shafts 18 of the belt pulleys 3 extend through the belt pulleys 3 and reach approximately level with body end of the drive motor 5. The second support wheels 11 are free to rotate mounted in bearings at the ends of said shafts 18. This embodiment has no ratchet mechanism, but instead, one of the belt pulleys 3 is mounted on its shaft 18 via a spring 14. This spring 14 performs during use the same function as the ratchet mechanism spring, yet the tensioning of the belt 2 in this embodiment is slightly more difficult than in the embodiment equipped with the ratchet mechanism 13. Also the insertion of the belt 2 onto the belt pulleys 3 is slightly more difficult, since the second support wheels 11 cannot be turned aside. On the other hand, this assembly has a simpler mechanical construction than in the assembly of the embodiment described first.

In addition to the above examples, the invention can have alternative embodiments.

The drive motor of the assembly can be easily provided with a pulse sensor or equivalent position indicator, whereby the location of the assembly on the perimeter of the pipe can be readily determined. The drive transmission chain from the motor 5 to the belt pulleys can be implemented by means of a belt or chain, and the motor can be adapted to rotate only one of the belt pulleys. Then, the motor can be placed within the belt pulley, for instance. Instead of the springloaded or lockable guide rollers, other means can be employed to secure the adherence of the belt to the perimeter of the belt pulley. The belt 2 resting against the pipe outer surface can be of different kinds. The essential requirement is that the belt is sufficiently wide and nonstretching in its longitudinal direction, and that it can be driven with the help of the belt pulleys without any essential slip. The belt outer surface resting against the pipe outer surface may be coated with a material exhibiting a high coefficient of friction. The belt length is advantageously dimensioned so that the slack leg does not become too long, while a free leg forming a longer loop as such has no detrimental effect on the function of the assembly. In principle the belt can be replaced by a chain, for example, but then the sideways guidance of the assembly must be provided by a separate guiding assembly.

The support wheels can be replaced by different types of rollers or even by glide surfaces. According to an interesting embodiment, a caterpillar track can be employed which is routed over the support wheels and for the length of its tensioned leg closely follows the pipe surface.

If the assembly is intended to carry an extremely heavy load, it can be designed for multiple transfer belts with respective belt pulleys to improve its load-carrying capacity. At the same time, the sideways stability is vastly enhanced by increasing the number of belts to, e.g., two belts alone. Alternatively, the above-described embodiment can be designed to use two narrow belts.

The assembly can be loaded with multiple different types of accessories. The most important herein is a transfer apparatus which can be used for transferring an ultrasonic transducer longitudinally, for example. Another interesting accessory could be a rechargeable battery system, whereby the cabling of the motor and the loading equipment cause no disturbance to the motion around the pipe. However, battery-powered operation is applicable to relatively lightweight assemblies only that can be operated from relatively small batteries. Owing to the large weight of high-capacity batteries, the use of rechargeable batteries is not possible in all locations.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

I claim:

1. An assembly for guiding different types of apparatuses around elongated objects having a circular cross section, said assembly comprising:
   a body part, and
   a motor for providing a transfer motion of the assembly, wherein
   a first and a second belt pulley are adapted to said body part and include shafts being aligned in parallel,
   a belt-like element capable of being adapted to run over said belt pulleys in the form of a folded loop, so that the loop opens between said belt pulleys, the loop section of said belt-like element an inner leg which rests against the periphery of said object of circular cross section, and
   means adapted to cooperate with each of said belt pulleys and suited for compressing said belt-like element essentially nonslipping against said pulley.

2. An assembly as defined in claim 1, wherein the beltlike element is a toothed belt and the belt pulleys are toothed belt pulleys.

3. An assembly as defined in claim 1, wherein the motor is geared to rotate both belt pulleys at synchronous speeds in the same direction of rotation.

4. An assembly as defined claim 1, wherein the elements for compressing the belt-like element against the belt pulleys are spring-loaded rollers.

5. An assembly as defined in claim 1, wherein the elements for compressing the belt-like element against the belt pulleys are rollers suited for locking against said belt.

6. An assembly as defined in claim 1, and further including a spring adapted at least one of the belt pulleys, whereby the spring provides the connection of said pulley to the drive shaft of said pulley.

7. An assembly as defined in claim 1, and further including a spring-loaded ratchet mechanism adapted at least one of the belt pulleys.

8. An assembly as defined in claim 1, and further including a pair of support wheels on which the assembly is adapted to run on the surface of the object.

9. An assembly as defined in claim 1, and further including a pulse transducer adapted to the motor for determining the position of the assembly during motion.

10. An assembly as defined in claim 3, wherein the motor is adapted between the belt pulleys and the rotational drive provided by the motor is geared to the belt pulleys from a driving gear wheel secured to the drive shaft of the motor via intermediate gear wheels adapted to both sides of the motor, said intermediate gear wheels being adapted to a meshing position with driven gear wheels secured to the shafts of the belt pulleys.

11. An assembly for guiding different types of apparatuses around elongated objects having a circular cross section, said assembly comprising:
   a body part, and
   a motor for providing a transfer motion of the assembly, wherein
   two pairs of belt pulleys, each said pair of belt pulleys including a first and a second pulley being adapted to said body part and include shafts being aligned in parallel,
   two pairs of belts, one of each of said pairs of belts being capable of being adapted to run over one corresponding pairs of belt pulleys in the form of a folded loop, so that the loop opens between said belt pulleys and that the loop section of said belts forming an inner leg rests against the periphery of said object of circular cross section, and
   means adapted to cooperate with each of said belt pulleys and suited for compressing said belts essentially nonslipping against said corresponding pulleys.

* * * * *